United States Patent
Yu et al.

(10) Patent No.: US 9,132,275 B2
(45) Date of Patent: Sep. 15, 2015

(54) AUTOMATIC DETERMINATION OF CHRONOTROPIC INCOMPETENCE USING ATRIAL PACING AT REST

(75) Inventors: Yinghong Yu, Shoreview, MN (US); Donald L. Hopper, Maple Grove, MN (US); Jiang Ding, Shoreview, MN (US); James O. Gilkerson, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 750 days.

(21) Appl. No.: 13/290,362

(22) Filed: Nov. 7, 2011

(65) Prior Publication Data

US 2012/0130440 A1     May 24, 2012

Related U.S. Application Data

(60) Provisional application No. 61/415,185, filed on Nov. 18, 2010.

(51) Int. Cl.
*A61N 1/36* (2006.01)
*A61N 1/368* (2006.01)

(52) U.S. Cl.
CPC .................................... *A61N 1/3682* (2013.01)

(58) Field of Classification Search
CPC .................................................... A61N 1/3682
USPC ............................................................ 607/2
See application file for complete search history.

(56) References Cited

U.S. PATENT DOCUMENTS

| | | |
|---|---|---|
| 4,773,401 A | 9/1988 | Citak et al. |
| 5,179,947 A | 1/1993 | Meyerson et al. |
| 5,309,919 A | 5/1994 | Snell et al. |
| 5,372,607 A * | 12/1994 | Stone et al. ............... 607/30 |
| 5,534,016 A | 7/1996 | Boute |
| 5,549,650 A | 8/1996 | Bornzin et al. |
| 5,713,930 A | 2/1998 | van der Veen et al. |
| 5,725,561 A | 3/1998 | Stroebel et al. |
| 5,735,880 A | 4/1998 | Prutchi et al. |
| 5,782,884 A | 7/1998 | Stotts et al. |
| 5,871,508 A | 2/1999 | Thompson et al. |
| 5,891,176 A | 4/1999 | Bornzin |
| 6,058,328 A | 5/2000 | Levine et al. |
| 6,076,015 A | 6/2000 | Hartley et al. |
| 6,190,324 B1 | 2/2001 | Kieval et al. |
| 6,361,522 B1 | 3/2002 | Scheiner et al. |
| 6,370,430 B1 | 4/2002 | Mika et al. |
| 6,377,851 B1 | 4/2002 | Shieh et al. |

(Continued)

*Primary Examiner* — Amanda Patton
(74) *Attorney, Agent, or Firm* — Schwegman Lundberg & Woessner, P.A.

(57) ABSTRACT

An apparatus comprises an implantable cardiac signal sensing circuit that provides an electrical cardiac signal representative of cardiac activity of a subject, an implantable therapy circuit that delivers electrical pacing stimulation energy to a heart of a subject, and a controller circuit. The controller circuit includes a chronotropic incompetence detection circuit that initiates pacing of an atrium of the subject at a rate higher than a device-indicated rate or a sensed intrinsic rate, monitor the AV interval, initiates an increase in the pacing rate while continuing the monitoring of the AV interval, calculates a change in AV intervals between a highest paced rate used in the monitoring and a lowest paced rate used in the monitoring, and indicates that the AV intervals are evidence of chronotropic incompetence when the calculated change in the AV intervals exceeds a specified threshold AV interval change value.

20 Claims, 4 Drawing Sheets

(56) References Cited

U.S. PATENT DOCUMENTS

| | | |
|---|---|---|
| 6,400,987 B1 | 6/2002 | Garberoglio |
| 6,529,771 B1 | 3/2003 | Kieval et al. |
| 6,604,000 B2 | 8/2003 | Lu |
| 6,628,985 B2 | 9/2003 | Sweeney et al. |
| 6,629,931 B1 | 10/2003 | Begemann et al. |
| 6,662,048 B2 | 12/2003 | Balczewski et al. |
| 6,689,117 B2 | 2/2004 | Sweeney et al. |
| 6,697,672 B2 | 2/2004 | Anderson |
| 6,704,602 B2 | 3/2004 | Berg et al. |
| 6,776,987 B1 | 8/2004 | Edelberg et al. |
| 6,795,733 B1 | 9/2004 | Lu |
| 6,858,006 B2 | 2/2005 | MacCarter et al. |
| 6,868,346 B2 | 3/2005 | Larson et al. |
| 6,904,311 B2 | 6/2005 | Freeberg |
| 6,911,209 B1 | 6/2005 | Lehtonen et al. |
| 6,970,742 B2 | 11/2005 | Mann et al. |
| 7,016,730 B2 | 3/2006 | Ternes |
| 7,050,854 B2 | 5/2006 | Daum et al. |
| 7,092,757 B2 | 8/2006 | Larson et al. |
| 7,142,920 B2 | 11/2006 | Scheiner et al. |
| 7,201,733 B2 | 4/2007 | Scheiner et al. |
| 7,269,458 B2 | 9/2007 | Kadhiresan et al. |
| 7,272,442 B2 | 9/2007 | Freeberg |
| 7,392,090 B2 | 6/2008 | Sweeney et al. |
| 7,425,210 B2 | 9/2008 | Sweeney et al. |
| 7,426,413 B2 | 9/2008 | Balczewski et al. |
| 7,483,743 B2 | 1/2009 | Mann et al. |
| 7,590,449 B2 | 9/2009 | Mann et al. |
| 7,599,741 B2 | 10/2009 | Hopper et al. |
| 7,606,616 B2 | 10/2009 | Daum et al. |
| 7,608,458 B2 | 10/2009 | Soykan et al. |
| 7,616,991 B2 | 11/2009 | Mann et al. |
| 7,620,446 B2 | 11/2009 | Ferek-Petric |
| 7,708,683 B2 | 5/2010 | Hadley |
| 7,717,854 B2 | 5/2010 | Mann et al. |

\* cited by examiner

AUTOMATIC DETERMINATION OF CHRONOTROPIC INCOMPETENCE USING ATRIAL PACING AT REST

CROSS-REFERENCE TO RELATED APPLICATIONS

This application claims the benefit of U.S. Provisional Application No. 61/415,185, filed on Nov. 18, 2010, under 35 U.S.C. §119(e), which is incorporated herein by reference in its entirety.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

Some IMDs detect events by monitoring electrical heart activity signals. In CFM devices, these events can include heart chamber expansions or contractions. By monitoring cardiac signals indicative of expansions or contractions, IMDs can detect abnormally slow heart rate, or bradycardia. In response to an abnormally slow heart rate some CFM devices deliver electrical pacing stimulation energy to induce cardiac depolarization and contraction (sometimes called capture of the heart). The stimulation energy is delivered to provide a depolarization rate that improves hemodynamic function of the patient.

Normally, a patient's heart rate changes in response to a change in physiologic need (e.g., exercise). However, some patients' ventricular depolarization rate may not adequately change in response to a change in physiologic demand. This condition is sometimes called chronotropic incompetence. The detection of chronotropic incompetence typically involves physician time with the patient in a clinic to conduct exertion tests to monitor a patient's response to exertion.

Examples of a cardiac device able to predict or recognize a chronotropically incompetent condition can be found in Scheiner et al., U.S. Pat. No. 7,142,920, "Chronotropic Status Monitor for Implantable Medical Device," filed May 25, 2004, which is incorporated herein by reference in its entirety. Examples of calibration of adaptive rate pacing using an intrinsic chronotropic response can be found in Daum et al., U.S. Pat. No. 7,050,854, "Calibration of Adaptive-Rate Pacing Using Chronotropic Response," filed Jun. 24, 2002, which is incorporated herein by reference in its entirety.

OVERVIEW

This document relates generally to systems, devices, and methods that provide electrical pacing therapy to the heart of a patient or subject. In particular it relates to systems, devices, and methods that detect when a patient or subject is chronotropically incompetent.

The present inventors have recognized, among other things, that testing for chronotropic incompetence can involve a complex series of tests in a clinical setting. Such testing is inconvenient for the patient and the physician. The present subject matter can provide a solution to this problem by simplifying the testing and making the testing more convenient for all involved.

An apparatus example comprises an implantable cardiac signal sensing circuit that provides an electrical cardiac signal representative of cardiac activity of a subject, an implantable therapy circuit that delivers electrical pacing stimulation energy to the heart of the subject, and a controller circuit. The controller circuit includes a chronotropic incompetence detection circuit that initiates pacing of an atrium of the subject at a rate higher than a device-indicated rate or a sensed intrinsic rate, monitor the AV interval, initiates an increase in the pacing rate while continuing the monitoring of the AV interval, calculates a change in AV intervals between a highest paced rate used in the monitoring and a lowest paced rate used in the monitoring, and indicates that the AV intervals are evidence of chronotropic incompetence when the calculated change in the AV intervals exceeds a specified threshold AV interval change value.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Chronotropic incompetence (CI) is common in patients who receive cardiac stimulators. CI is the inability to increase intrinsic heart rate appropriately in response to an increase in physiologic need of the patient. Patients with CI may need cardiac stimulation therapy different from patients without CI. For example, a physician may prescribe a pacemaker with adaptive rate pacing for a patient with CI. An adaptive rate pacemaker typically includes a sensor to sense a change in physiologic need of the patient. The pacemaker then adjusts the pacing rate according to indications provided by the sensor of the change in physiologic need.

In general, a patient is identified as being chronotropically incompetent though clinical testing. This testing may involve determining the patient's response to exercise, which can be a complex and time consuming process. An automated device test would be more convenient for the patient and would reduce the costs associated with clinical testing of the patient.

Figure 1:
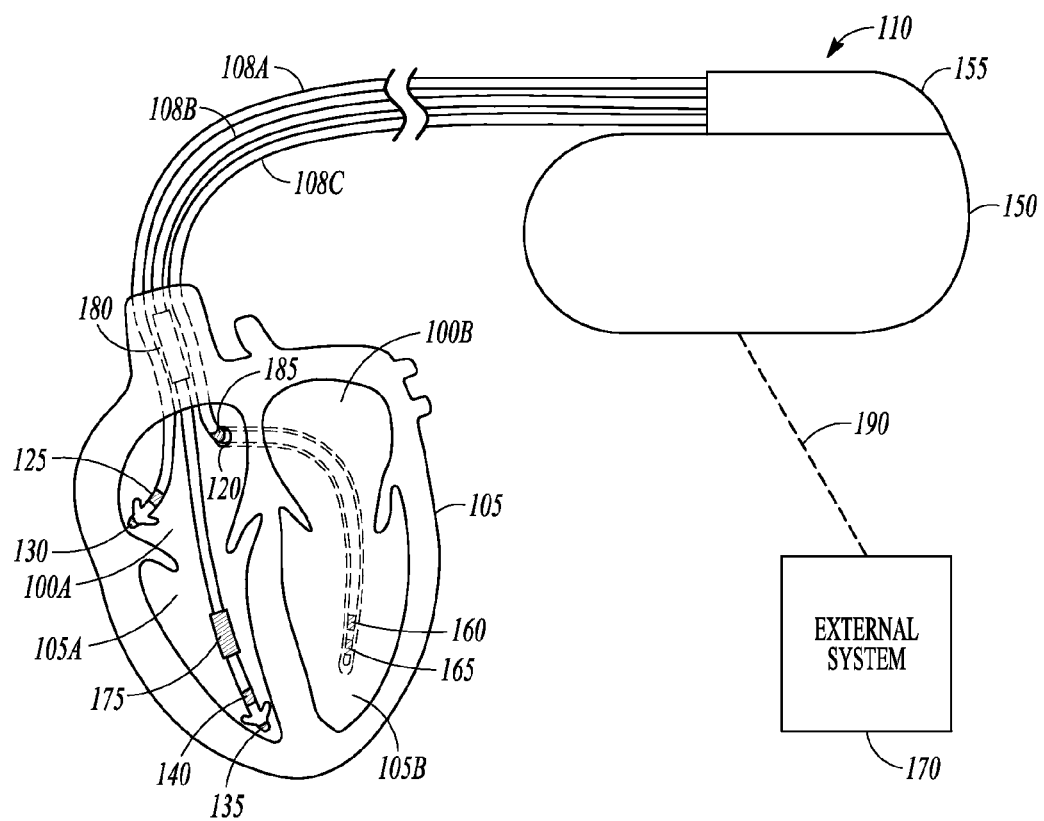
FIG. 1 is an illustration of an example of portions of a system that includes an IMD.

FIG. 1 is an illustration of portions of a system that uses an IMD 110. Examples of IMD 110 include, without limitation, a pacer, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 is coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Sensed electrical cardiac signals can be sampled to create an electrogram (sometimes called an egram). An electrogram can be analyzed by the IMD and/or can be stored in the IMD and later communicated to an external device where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 may include a third cardiac lead 108C attached to the IMD 110 through the header 155. The third cardiac lead 108C includes electrodes 160 and 165 placed in a coronary vein lying epicardially on the left ventricle (LV) 105B via the coronary vein. The third cardiac lead 108C may include a ring electrode 185 positioned near the coronary sinus (CS) 120.

Lead 108B may include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Other forms of electrodes include meshes and patches which may be applied to portions of heart 105 or which may be implanted in other areas of the body to help "steer" electrical currents produced by IMD 110. An IMD may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Note that although a specific arrangement of leads and electrodes are shown the illustration, the present methods and systems will work in a variety of configurations and with a variety of electrodes.

Figure 2:
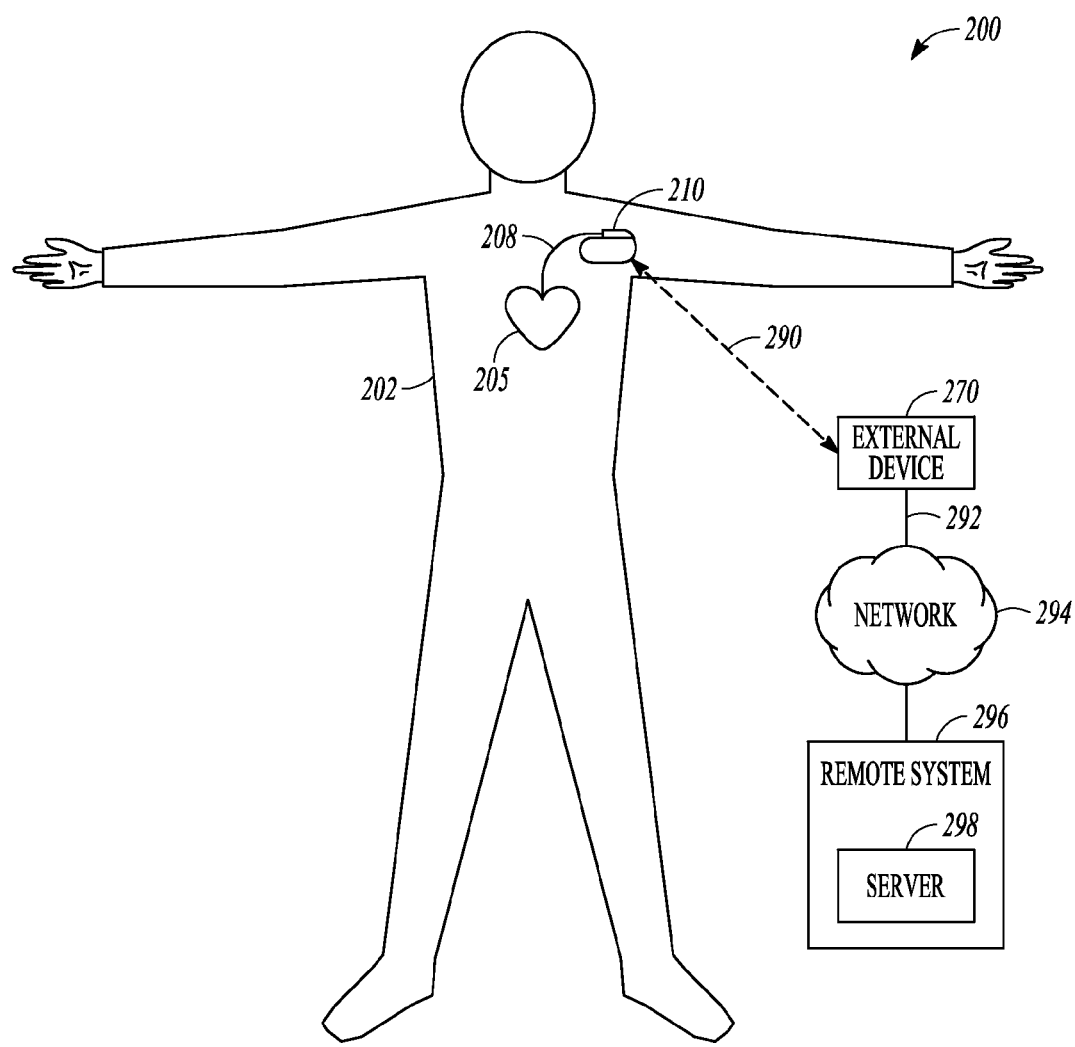
FIG. 2 is an illustration of another example of portions of a system that includes an IMD.

FIG. 2 is an illustration of portions of another system 200 that uses an IMD 210 to provide a therapy to a patient 202. The system 200 typically includes an external device 270 that communicates with a remote system 296 via a network 294. The network 294 can be a communication network such as a phone network or a computer network (e.g., the internet). In some examples, the external device 270 includes a repeater and communicates via the network 294 using a link 292 that may be wired or wireless. In some examples, the remote system 296 provides patient management functions and may include one or more servers 298 to perform the functions.

This document describes a device based method that automatically determines whether a patient is chronotropically incompetent. In one example, the medical device tests include pacing the patient's heart and incrementally increasing the pacing rate while monitoring the time interval between an atrial depolarization and a ventricular depolarization (AV interval). CI can be detected by monitoring the changes in AV interval during the pacing.

Figure 3:
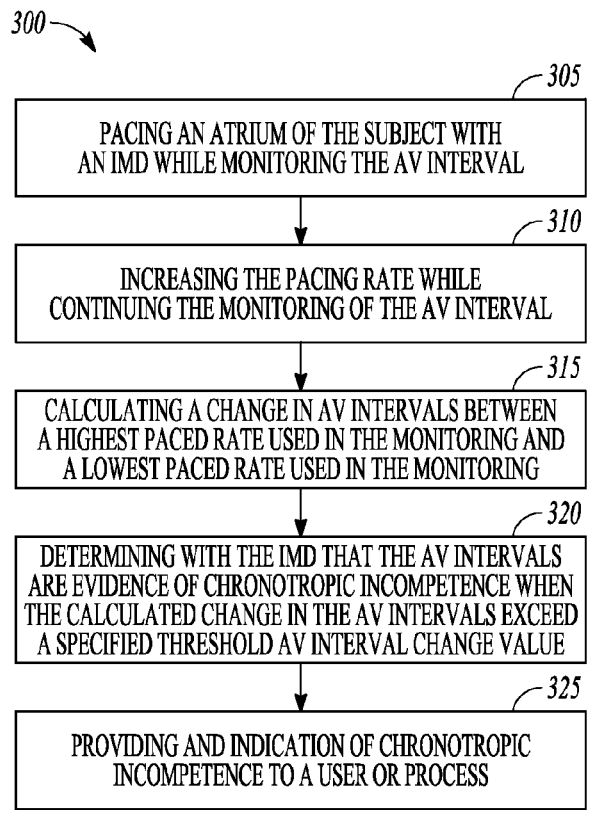
FIG. 3 is a flow diagram of an example of a method of detecting chronotropic incompetence using a medical device.

FIG. 3 is a flow diagram of an example of a method 300 of detecting CI using a medical device, such as an IMD. A test for CI may be initiated by the IMD or by an external device. At block 305, pacing therapy is provided to an atrium of the subject with the IMD while monitoring a time interval between a paced event in the atrium and a sensed intrinsic event in the ventricle (AV interval). Either one or both of the right ventricle and the left ventricle may be monitored.

In some examples, the initial paced rate of the test is higher than a sensed intrinsic rate of the patient. In some examples, the paced rate is increased from a device indicated rate, such as a device programmed rate or a sensor indicated rate.

At block 310, the pacing rate is increased while the monitoring of the AV interval is continued. The pacing rate can be increased incrementally to track incremental changes in AV interval during the test. In some examples, the IMD continues to incrementally increase the pacing rate until a specified heart rate is reached. In certain examples, the specified heart rate is a programmed rate for the end of the test (e.g., 130 beats per minute (bpm)).

At block 315, a change in AV intervals is calculated between a highest paced rate used in the monitoring and a lowest paced rate used in the monitoring. The ventricles of a patient with CI are likely to have larger calculated changes in AV intervals than a patient without CI. In some examples, the calculation includes only those AV intervals that meet a qualification criterion (e.g., only those AV intervals that are deemed stable are included).

In some examples, the degree or severity of the CI of the patient is determined using the AV intervals. The magnitude of the AV interval change can be proportional to the degree of CI. In some examples, a measured magnitude of one or more AV interval change values is compared to one or more interval threshold values to determine the patient's degree of CI.

At block 320, the AV intervals are determined to be evidence of CI when the calculated change in the AV intervals exceeds a specified threshold AV interval change value. At block 325, an indication of CI is provided to a user or process. In some examples, the indication is provided to a process executing on a medical device (e.g., the IMD). The indication may be used by the process to initiate or change a therapy provided to the patient. In some examples, the indication is communicated to a second device having a display so that a user can be notified of the classification.

Figure 4:
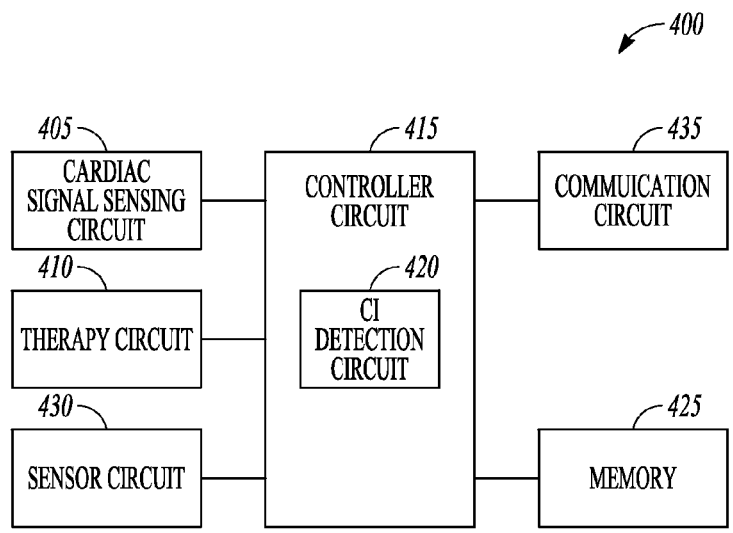
FIG. 4 is a block diagram of portions of an example of a device to automatically detect chronotropic incompetence of a patient or subject.

FIG. 4 is a block diagram of portions of an example of a device 400 to automatically detect CI of a patient or subject. The device 400 includes an implantable cardiac signal sensing circuit 405 that provides an electrical cardiac signal representative of cardiac activity of the subject. In some examples, the cardiac signal sensing circuit 405 detects cardiac depolarization in the sensed cardiac signal. In certain examples, the cardiac signal sensing circuit 405 includes a peak detector to detect a QRS complex in the sensed cardiac signal that is representative of depolarization of one or both of the subject's ventricles. The device 400 also includes an implantable therapy circuit 410 that delivers electrical pacing stimulation energy to the heart of the subject.

The device 400 further includes a controller circuit 415 that is communicatively coupled to the cardiac signal sensing circuit 405 and the therapy circuit 410. The communicative coupling allows for communication of electronic signals between the controller circuit 415, the cardiac signal sensing circuit 405, and the therapy circuit 410 even though there may be intervening circuitry between them in the device 400.

The controller circuit 415 may include a processor such as a microprocessor, a digital signal processor, application specific integrated circuit (ASIC), microprocessor, or other type of processor, interpreting or executing instructions in software or firmware. The controller circuit 415 includes other circuits or sub-circuits to perform the functions described. These circuits may include software, hardware, firmware or any combination thereof. Multiple functions can be performed in one or more of the circuits as desired.

The controller circuit 415 includes a CI detection circuit 420 that executes a CI test. To perform the CI test, the CI detection circuit 420 initiates pacing of an atrium of the subject at a rate higher than a device-indicated rate or sensed intrinsic depolarization rate and monitors a time interval between a paced event in the atrium and a sensed intrinsic event in the ventricle (AV interval). In some examples, the cardiac signal sensing circuit 405 is electrically connectable to an electrode configured for placement in or near a left ventricle and the AV interval includes the interval from an atrial paced depolarization to a left ventricular sensed depolarization. Examples of such an electrode include electrodes 160 and 165 in FIG. 1. In some examples, the cardiac signal sensing circuit 405 is electrically connectable to an electrode configured for placement in or near a right ventricle and the AV interval includes the interval from an atrial paced depolarization to a right ventricular sensed depolarization. Examples of such an electrode include electrodes 135, 140, and 175 in FIG. 1. In some examples, the CI detection circuit 420 monitors AV intervals that include events sensed in both the right and left ventricles.

To continue the test for CI, the CI detection circuit 420 initiates an increase in the pacing rate while continuing the monitoring of the AV interval. In some examples, the pacing rate is incrementally increased (e.g., by steps of 10 pm) and the AV interval is measured at each step.

In some examples, the CI detection circuit 420 continues to increase the pacing rate and measure the AV intervals until a specified pacing rate is reached. In some examples, the device 400 includes a memory 425 communicatively coupled to or integral to the controller circuit 415. In certain examples, the specified pacing rate is an end of test rate programmed into the memory 425. In certain examples, the specified pacing rate is a maximum pacing rate programmed in the memory 425. In certain examples, the specified pacing rate is a maximum age-dependent rate programmed in the memory 425. This rate is a statistically determined maximum heart rate for someone of the patient's age. In some examples, the specified pacing rate is a programmed maximum tracking rate. The maximum tracking rate is the fastest atrial depolarization rate at which consecutively paced ventricular depolarizations maintain one-to-one (1:1) synchrony with sensed atrial events. When the specified pacing rate is reached, the controller circuit 415 either sets the pacing rate below the previously sensed intrinsic rate of the subject or returns to delivering pacing therapy at the device-indicated rate (e.g., the pacing lower rate limit).

In some examples, the CI detection circuit 420 continues to increase the pacing rate and measure the AV intervals until determining that the AV intervals have become unstable during the test. In certain examples, the CI detection circuit 420 determines that the AV intervals are unstable when a loss of 1:1 conduction from the atrium to the ventricle is sensed. In certain examples, the CI detection circuit 420 calculates a central tendency (e.g., a mean value or median value) of measured AV intervals and a standard deviation of measured AV intervals. The CI detection circuit 420 determines that the AV intervals are unstable when the calculated standard deviation becomes at least twenty percent of the calculated central tendency. In certain examples, the CI detection circuit 420 determines that the AV intervals are unstable by the earlier of i) a sensed loss of 1:1 conduction from the atrium to the ventricle and ii) the calculated AV interval standard deviation becoming at least twenty percent of the calculated AV interval central tendency. In some examples, the controller circuit 415 stores the atrial pacing rate or the pacing interval at which the AV intervals become unstable. This information can be later retrieved from the device.

When the CI detection circuit 420 has finished incrementing the pacing, the CI detection circuit 420 calculates a change in AV intervals between the highest paced rate used in the monitoring and the lowest paced rate used in the monitoring. In some examples, only AV interval measurements prior to the AV interval becoming unstable are deemed as valid AV intervals and are used to calculate the change in AV intervals between the highest paced rate and the lowest paced rate.

In some examples, the CI detection circuit 420 indicates that the AV intervals are evidence of CI when the calculated change in the AV intervals exceeds a specified threshold AV interval change value (e.g., the AV interval changes 80 milliseconds (80 ms) for a heart rate change of 40 bpm during the test). The specified threshold AV interval change value may be a value determined for an individual patient. In certain examples, the specified threshold is a value determined statistically from a patient population.

In some examples, the CI detection circuit 420 monitors the change in AV intervals as a function of the paced rate during the test (e.g., change in AV interval in ms versus heart rate in bpm). Alternatively, the CI detection circuit 420 may monitor the change in AV intervals as a function of the time interval between atrial paces (e.g., change in AV interval in ms versus AA interval in ms).

The CI detection circuit 420 then calculates a slope of the change in AV intervals versus paced rate (or paced interval) during the test. The CI detection circuit 420 provides an indication of CI when the calculated slope exceeds a specified slope value.

Figure 5:
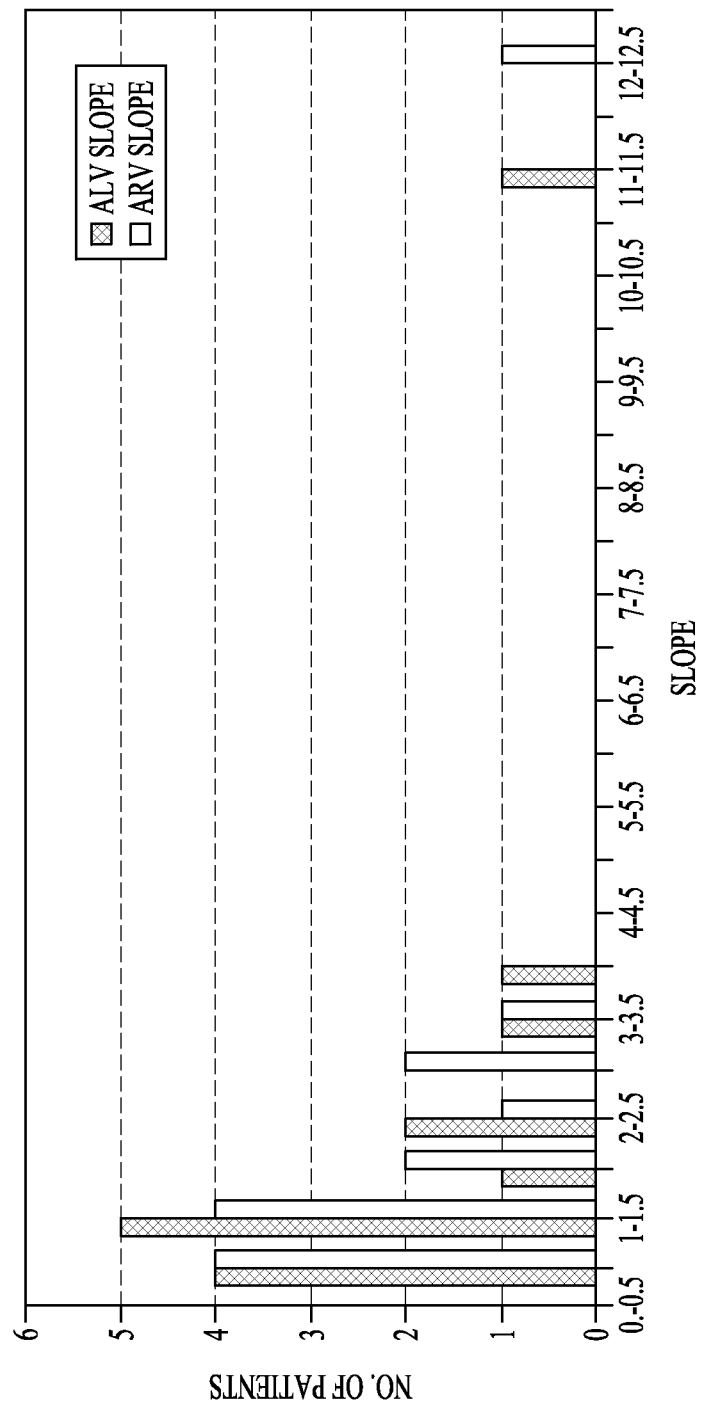
FIG. 5 shows a graph of calculated AV interval change slopes of a sampling of patients with cardiac stimulation devices.

FIG. 5 shows a graph of calculated slopes of a sampling of patients with cardiac stimulation devices. Those patients with slopes of 2 (slope of 2=$\Delta$2 ms/bpm) or higher may be deemed by the CI detection circuit 420 to have CI.

In some examples, the CI detection circuit 420 calculates the slope using the change in AV interval and the change in AA interval (e.g., $\Delta AV/\Delta AA$) from the first paced rate to the last valid paced rate. In some examples, the CI detection circuit 420 calculates the slope of the change in AV intervals by calculating a slope of a fitted AV interval versus heart rate curve using valid AV interval measurements (e.g., measurements from those AV intervals that are stable).

When the CI test is complete, the controller circuit 415 may provide an indication of CI to a user or process. In some examples, the indication of CI is stored in memory 425 and is read by a second device. In some examples, device includes a communication circuit 435 communicatively coupled to the controller circuit 415. The controller circuit 415 is configured to communicate or provide an alert to a second device according to the indication of CI. The second device may present the alert to a user.

According to some examples, the CI detection circuit 420 determines a degree of severity of the CI. The CI detection circuit 420 may compare the calculated change in AV interval to a plurality of specified threshold AV interval change values; each value corresponding to a degree of severity of CI. For example, the 80 ms example value given above may be used to deem that the CI of the subject is severe. Lesser change values (e.g., 20 ms over a heart rate change of at least 40 bpm) may be used to deem that the CI of the subject is not severe, and larger change values (e.g., 160 ms) may be used to deem that the CI of the subject is very severe.

In some examples, the CI detection circuit 420 compares a calculated value of slope of the change in AV intervals to a plurality of specified AV interval slope values. For example, the $\Delta$2 ms/bpm example value given above may be used to deem that the CI of the subject is severe. Lesser change values (e.g., $\Delta$1 ms/bpm) may be used to deem that the CI of the subject is not severe, and larger change values (e.g., $\Delta$4 ms/bpm) may be used to deem that the CI of the subject is very severe.

The CI detection circuit can provide an indication of the degree of severity of the CI according to the comparison. In some examples, the indication includes the likelihood that the subject has heart disease based on the indication of CI. In some examples, the likelihood of heart disease is quantified using the determined severity of the CI.

In some examples, the calculated slope is trended over time to track changes in CI severity. In certain examples, the calculated slope is communicated to an external device and the slope is trended at a server that is part of a remote patient management system. In certain examples, the slope is trended using the memory 425 of the device. Specified changes in the trending detected by the controller circuit 415 may trigger a communication of an indication of the severity of the CI to an external device.

When the severity of CI of the subject is determined, the CI detection circuit 420 may change a parameter of the CI testing according to the indication of CI severity. In some examples, the testing parameter is the frequency of performing the CI testing. The controller circuit 415 recurrently initiates the pacing and monitoring as part of a scheduled CI detection test. The controller circuit 415 may change the frequency of initiating the CI detection test according to the indicated severity of CI. For examples, if the CI is deemed to be severe by the CI detection circuit 420, the controller circuit 415 may increase the frequency with which the tests are run. If the CI is deemed to be less severe by the CI detection circuit 420, the controller circuit 415 may decrease the frequency with which the tests are run. Thus, the frequency of the CI tests may change by the controller circuit 415 according to the determined severity of CI of the subject.

According to some examples, the device 400 provides adaptive rate pacing. The device 400 may include a sensor circuit 430 communicatively coupled to the controller circuit 415. The sensor circuit 430 provides an electrical signal representative of a physiologic parameter of the subject. Changes in the sensor electrical signal can indicate a physiologic need for a change in the subject's heart rate. To provide adaptive rate pacing, the controller circuit 415 adjusts a pacing rate according to the electrical signal provided by the sensor circuit 430.

In some examples, the sensor circuit 430 includes an accelerometer. An accelerometer can provide an electrical signal representative of sensed acceleration of a patient's body. Sensed acceleration can be used to detect patient activity or exercise, and thus sense a physiologic need for a change in heart rate. The controller circuit 415 initiates delivery of pacing therapy having a pacing rate or interval that is a function of the signal from the accelerometer. Examples of an accelerometer-based rate adaptive pacemaker are described in Meyerson et al., U.S. Pat. No. 5,179,947, entitled "Acceleration-Sensitive Cardiac Pacemaker and Method of Operation," filed Jan. 15, 1991, which is incorporated herein by reference in its entirety.

In some examples, the sensor circuit 430 includes a transthoracic impedance sensor. A transthoracic impedance sensor measures impedance across the thorax region of a patient. This impedance measurement can be used to derive lung tidal volume for the subject. Changes in lung tidal volume can be used to deduce a physiologic need for change in heart rate of the patient. To measure impedance, a predetermined excitation current is delivered between the electrodes and the impedance is determined from a voltage sensed between the electrodes. Transthoracic impedance can be measured between an electrode in the right ventricle (e.g., ring electrode 140 in FIG. 1) and an electrode formed on the can 150 an electrode formed on the header 155. Examples of methods of monitoring lung tidal volume by measuring transthoracic impedance are described in Hartley et al., U.S. Pat. No. 6,076, 015 entitled "Rate Adaptive Cardiac Rhythm Management Device Using Transthoracic Impedance," filed Feb. 27, 1998, which is incorporated herein by reference in its entirety.

In some examples, the sensor circuit 430 includes an intracardiac impedance sensor. Intracardiac impedance can be measured between electrodes positioned within the right ventricle of the heart. This intracardiac impedance signal can be processed to obtain a measure of the time interval beginning with a paced or spontaneous QRS complex (systole marker) and ending with a point where the impedance signal crosses the zero axis in the positive direction following the QRS complex. The time interval may decrease with exercise and thus sense a physiologic need for a change in heart rate. Systems and methods to measure intracardiac impedance are described in Citak et al., U.S. Pat. No. 4,773,401, entitled "Physiologic Control of Pacemaker Rate Using Pre-Ejection Interval as the Controlling Parameter," filed Aug. 21, 1987, which is incorporated herein by reference.

In some examples, the sensor circuit 430 includes a temperature sensor that provides a sensor signal representative of body temperature of a patient. A change in temperature may be indicative of a physiologic need for a change in heart rate (e.g., a temperature change due to activity).

In some examples, a physiologic need for a change in heart rate is determined using the cardiac signal sensing circuit 405 or a second cardiac signal sensing circuit included in the sensor circuit 430. The sensor signal includes a representation of a depolarization interval that includes a QRST complex. A QRST complex represents ventricular depolarization and repolarization. A change in the polarization of the interval from the Q-wave to the T-wave (QT interval) may be indicative of a physiologic need for a change in heart rate.

According to some examples, when the CI detection circuit 420 detects that a subject has CI, the indication of CI is used by the controller circuit 415 to activate adaptive rate pacing in the device 400. In some examples, when the CI detection circuit 420 generates an indication of the severity of the CI, the controller circuit 415 may determine a value of a programmable parameter related to adaptive rate pacing according to the indicated severity of CI.

The parameter related to adaptive rate pacing may include at least one of a rate response factor, a sensitivity setting of a sensor circuit, a maximum sensor indicated rate, a lower rate limit, and a rate-responsive mode of the controller circuit (e.g., the NASPE/BERG defined DDDR mode).

In certain examples, the controller circuit 415 provides an alert of CI of the subject and the alert includes the determined value of the programmable parameter related to adaptive rate pacing. This alert can be communicated to a second device for display to a user. The second device may be an external programmer and the user may then decide to change the programmable parameter to the determined value. In certain examples, the controller circuit 415 automatically updates the programmable parameter to the determined value.

According to some examples, the controller circuit 415 recurrently initiates the pacing and monitoring as part of a scheduled CI detection test. In some examples, it may be desired for the device 400 to perform the test while the subject is at rest. The controller circuit 415 detects when the subject is at rest and initiates the CI detection test while the subject is at rest. The controller circuit 415 may detect that the subject is at rest when the sensed intrinsic rate or interval of the subject is at or below a specified threshold rate or interval. As described above, the device 400 may include a sensor circuit 430 to detect subject activity or exercise. The controller circuit 415 may deduce that the subject is at rest based on the sensor signal provided by the sensor circuit 430.

In some examples, it may be desired for the device 400 to perform the test while the subject is active. The controller circuit 415 may detect when the subject is active and initiate the CI detection test while the subject is active. The controller circuit 415 may detect that the subject is active using the sensed intrinsic rate or interval, and/or may detect that the subject is active using a signal provided from the sensor circuit 430.

According to some examples, the memory 425 stores an indication of a drug therapy of the subject. The drug therapy may include a drug that causes the subject to experience some degree of CI. An example of such a drug is a β-adrenergic blocking drug, sometimes called a beta blocker. A beta blocker may reduce sympathetic responsiveness of heart rate in a patient. It may be desirable to monitor CI of a patient undergoing such a drug therapy to monitor the effect of the drug. Based on a determined severity of CI, the controller circuit 415 may provide an alert of CI of the subject. The alert may include a recommendation to adjust the drug therapy of the subject according to the indicated severity of CI. If the CI is deemed to be too severe, the alert may include a recommendation to reduce the amount of drug provided by the drug therapy. If the CI is deemed to be low in the patient (e.g., the calculated slope is very low, such as a slope in the range of $\Delta 0$ ms/bpm to $\Delta 1$ ms/bpm), the alert may recommend increasing the amount of drug because the subject's tolerance of the drug may have increased.

In some examples, the controller circuit 415 changes a frequency of performing the CI test based on the indication of drug therapy stored in memory 425. In certain examples, the controller circuit 415 initiates CI testing more often when drug therapy is indicated than when drug therapy is not indicated. The indication of drug therapy stored in memory may include an indication that drug therapy was changed. In certain examples, the controller circuit 415 initiates CI testing more often when the indication is that drug therapy was changed than when no change in drug therapy is indicated.

Use of an automated test for CI is more convenient for the patient and reduces the cost of clinic time for existing detection methods.

ADDITIONAL NOTES

This document describes systems, devices, and methods that detect when a patient or subject is chronotropically incompetent.

Example 1 includes subject matter (such as an apparatus) comprising an implantable cardiac signal sensing circuit configured to provide an electrical cardiac signal representative of cardiac activity of a subject, an implantable therapy circuit configured to deliver electrical pacing stimulation energy to a heart of a subject, and a controller circuit, communicatively coupled to the cardiac signal sensing circuit and the therapy circuit, including a chronotropic incompetence detection circuit. The chronotropic incompetence detection circuit is configured to initiate pacing of an atrium of the subject at a rate higher than a device-indicated rate or a sensed intrinsic rate, monitor a time interval between a paced event in the atrium and a sensed intrinsic event in the ventricle (AV interval), initiate an increase in the pacing rate while continuing the monitoring of the AV interval, calculate a change in AV intervals between a highest paced rate used in the monitoring and a lowest paced rate used in the monitoring, indicate that the AV intervals are evidence of chronotropic incompetence when the calculated change in the AV intervals exceeds a specified threshold AV interval change value, and provide an indication of chronotropic incompetence to a user or process.

In Example 2, the chronotropic incompetence detection circuit of Example 1 can optionally be configured to determine a severity of the chronotropic incompetence according to a comparison of the calculated change to a plurality of specified threshold AV interval change values.

In Example 3, the chronotropic incompetence detection circuit of one or any combination of Examples 1 and 2 can optionally be configured to monitor AV intervals as a function of the paced rate, calculate a slope of the change in AV intervals, and provide an indication of chronotropic incompetence when the calculated slope exceeds a specified slope value.

In Example 4, the chronotropic incompetence detection circuit of one or any combination of examples 1-3 can optionally be configured to calculate the slope of the change in AV intervals by calculating a slope of a curve fitted to valid AV interval measurements.

In Example 5, the chronotropic incompetence detection circuit of one or any combination of Examples 1-4 can optionally be configured to compare the calculated slope to a plurality of specified AV interval slope values, and indicate a severity of the chronotropic incompetence of the subject according to the comparison.

In Example 6, the controller circuit of one or any combination of Examples 1-5 can be optionally configured to determine a value of a programmable parameter related to adaptive rate pacing according to the indicated severity of chronotropic incompetence, and provide an alert of chronotropic incompetence of the subject, wherein the alert includes the value of the programmable parameter.

In Example 7, the parameter related to adaptive rate pacing of one or any combination of Examples 1-6 can optionally include at least one of a rate response factor, a sensitivity of a sensor circuit communicatively coupled to the controller circuit, wherein the sensor circuit provides an electrical signal representative of a physiologic parameter of the subject, a maximum sensor indicated rate, a rate-responsive mode of the controller circuit, and a lower rate limit.

In Example 8, the controller circuit of one or any combination of Examples 1-7 can be optionally configured to determine a value of a programmable parameter related to adaptive rate pacing according to the indicated severity of chronotropic incompetence, and update the programmable parameter to the determined value.

In Example 9, the subject matter of one or any combination of Examples 1-8 can optionally include a memory communicatively coupled to or integral to the controller circuit and configured to store an indication of a drug therapy of the subject, wherein the controller circuit can optionally be configured to provide an alert of chronotropic incompetence of the subject, and wherein the alert can optionally include a recommendation to adjust the drug therapy of the subject according to the indicated severity of chronotropic incompetence.

In Example 10, the controller circuit of one or any combination of Examples 1-9 can optionally be configured to recurrently initiate the pacing and monitoring as part of a scheduled chronotropic incompetence detection test, and change a frequency of initiating the chronotropic incompetence detection test according to the indicated severity of chronotropic incompetence.

In Example 11, the controller circuit of one or any combination of Examples 1-10 can optionally be configured to recurrently initiate the pacing and monitoring as part of a scheduled chronotropic incompetence detection test, detect when the subject is at rest, and initiate the chronotropic incompetence detection test while the patient is at rest.

In Example 12, the controller circuit of one or any combination of Examples 1-11 can optionally be configured to recurrently initiate the pacing and monitoring as part of a scheduled chronotropic incompetence detection test, detect when the subject is active, and initiate the chronotropic incompetence detection test while the patient is active.

In Example 13, the controller circuit of one or any combination of Examples 1-12 can optionally be configured to provide an alert that includes a likelihood that the subject has heart disease based on the indication of chronotropic incompetence.

In Example 14, the subject matter of one or any combination of Examples 1-13 can optionally include a sensor circuit communicatively coupled to the controller circuit, wherein the sensor circuit provides an electrical signal representative of a physiologic parameter of the subject, and wherein the controller circuit is configured to adjust a pacing rate according to the electrical signal provided by the sensor circuit.

In Example 15, the sensor circuit of Example 14 can optionally include at least one of an accelerometer, an intracardiac impedance sensor, a transthoracic impedance sensor, a temperature sensor, wherein the sensor signal is representative of body temperature of the subject, and the cardiac signal sensing circuit, wherein the sensor signal includes a representation of a depolarization interval that includes a QRS complex.

In Example 16, the controller circuit of one or any combination of Examples 1-15 can optionally be configured to initiate pacing at the device-indicated rate or set the pacing rate below the sensed intrinsic rate when a specified pacing rate is reached during the monitoring or when the AV interval of the subject becomes unstable during the monitoring.

In Example 17, the chronotropic incompetence detection circuit of one or any combination of Examples 1-16 can optionally be configured to continue to increase the pacing and monitor the AV interval until the AV interval of the subject becomes unstable during the monitoring, wherein the controller circuit is configured to store at least one of the rate or the interval at which the atrium is paced when the AV interval becomes unstable, and wherein only AV intervals prior to the AV interval becoming unstable are deemed as valid AV intervals and are used to calculate the change in AV intervals between the highest paced rate and the lowest paced rate used in the monitoring.

Example 18 can include subject matter, or can optionally be combined with the subject matter of one or any combination of Examples 1-17 to include subject matter (such as a method, a means for performing acts, or a machine-readable medium including instructions that, when performed by the machine, cause the machine to perform acts), comprising pacing an atrium of the subject with an IMD while monitoring an AV interval where the paced rate is higher than a device-indicated rate or sensed intrinsic rate, increasing the pacing rate while continuing the monitoring of the AV interval, calculating with the IMD a change in AV intervals between a highest paced rate used in the monitoring and a lowest paced rate used in the monitoring, determining with the IMD that the AV intervals are evidence of chronotropic incompetence when the calculated change in the AV intervals exceeds a specified threshold AV interval change value, and providing an indication of chronotropic incompetence to a user or process.

In Example 19, the determining that the AV intervals are evidence of chronotropic incompetence of Example 18 can optionally include determining a severity of the chronotropic incompetence according to a comparison of the calculated change to a plurality of specified threshold AV interval change values.

In Example 20, the subject matter of one or any combination of Examples 18 and 19 can optionally include monitoring AV intervals as a function of paced rate, the calculating a change in the AV intervals can optionally include calculating a slope of the change in AV intervals, and the determining that the AV intervals are evidence of chronotropic incompetence can optionally include determining that the AV intervals are evidence of chronotropic incompetence when the calculated slope exceeds a specified slope value.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a tangible and/or non-transitory computer-readable medium or machine-readable medium encoded with instructions operable to configure an electronic device to perform methods as described in the above examples. An implementation of such methods can include software or code, such as microcode, assembly language code, a higher-level language code, or the like. Such code can include computer readable instructions for performing various methods. The code can form portions of computer program products. Further, the code can be tangibly stored on one or more volatile or non-volatile tangible computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
    an implantable cardiac signal sensing circuit configured to provide an electrical cardiac signal representative of cardiac activity of a subject;
    an implantable therapy circuit configured to deliver electrical pacing stimulation energy to a heart of a subject; and
    a controller circuit, communicatively coupled to the cardiac signal sensing circuit and the therapy circuit, including a chronotropic incompetence detection circuit configured to:
        initiate pacing of an atrium of the subject at a rate higher than a device-indicated rate or a sensed intrinsic rate;
        monitor a time interval between a paced event in the atrium and a sensed intrinsic event in the ventricle (paced AV interval);
        initiate an increase in the pacing rate while continuing the monitoring of the paced AV interval;
        calculate a change in paced AV intervals between a highest paced rate used in the monitoring and a lowest paced rate used in the monitoring;
        indicate that the paced AV intervals are evidence of chronotropic incompetence when the calculated change in the paced AV intervals exceeds a specified threshold AV interval change value; and
        provide an indication of chronotropic incompetence to a user or process.

2. The apparatus of claim 1, wherein the chronotropic incompetence detection circuit is configured to determine a severity of the chronotropic incompetence according to a comparison of the calculated change to a plurality of specified threshold AV interval change values.

3. The apparatus of claim 1, wherein the chronotropic incompetence detection circuit is configured to:
    monitor AV intervals as a function of the paced rate;
    calculate a slope of the change in AV intervals; and
    provide an indication of chronotropic incompetence when the calculated slope exceeds a specified slope value.

4. The apparatus of claim 3, wherein the chronotropic incompetence detection circuit is configured to calculate the slope of the change in AV intervals by calculating a slope of a curve fitted to valid AV interval measurements.

5. The apparatus of claim 3, wherein the chronotropic incompetence detection circuit is configured to:
compare the calculated slope to a plurality of specified AV interval slope values; and
indicate a severity of the chronotropic incompetence of the subject according to the comparison.

6. The apparatus of claim 5, wherein the controller circuit is configured to:
determine a value of a programmable parameter related to adaptive rate pacing according to the indicated severity of chronotropic incompetence; and
provide an alert of chronotropic incompetence of the subject, wherein the alert includes the value of the programmable parameter.

7. The apparatus of claim 6, wherein the parameter related to adaptive rate pacing includes at least one of:
a rate response factor;
a sensitivity of a sensor circuit communicatively coupled to the controller circuit, wherein the sensor circuit provides an electrical signal representative of a physiologic parameter of the subject;
a maximum sensor indicated rate;
a rate-responsive mode of the controller circuit; and
a lower rate limit.

8. The apparatus of claim 5, wherein the controller circuit is configured to:
determine a value of a programmable parameter related to adaptive rate pacing according to the indicated severity of chronotropic incompetence; and
update the programmable parameter to the determined value.

9. The apparatus of claim 5, including:
a memory, communicatively coupled to or integral to the controller circuit, wherein the memory is configured to store an indication of a drug therapy of the subject,
wherein the controller circuit is configured to provide an alert of chronotropic incompetence of the subject, and
wherein the alert includes a recommendation to adjust the drug therapy of the subject according to the indicated severity of chronotropic incompetence.

10. The apparatus of claim 5, wherein the controller circuit is configured to:
recurrently initiate the pacing and monitoring as part of a scheduled chronotropic incompetence detection test, and
change a frequency of initiating the chronotropic incompetence detection test according to the indicated severity of chronotropic incompetence.

11. The apparatus of claim 1, wherein the controller circuit is configured to:
recurrently initiate the pacing and monitoring as part of a scheduled chronotropic incompetence detection test;
detect when the subject is at rest; and
initiate the chronotropic incompetence detection test while the patient is at rest.

12. The apparatus of claim 1, wherein the controller circuit is configured to:
recurrently initiate the pacing and monitoring as part of a scheduled chronotropic incompetence detection test;
detect when the subject is active; and
initiate the chronotropic incompetence detection test while the patient is active.

13. The apparatus of claim 1, wherein the controller circuit is configured to provide an alert that includes a likelihood that the subject has heart disease based on the indication of chronotropic incompetence.

14. The apparatus of claim 1, including:
a sensor circuit communicatively coupled to the controller circuit, wherein the sensor circuit provides an electrical signal representative of a physiologic parameter of the subject, and
wherein the controller circuit is configured to adjust a pacing rate according to the electrical signal provided by the sensor circuit.

15. The apparatus of claim 14, wherein the sensor circuit includes at least one of:
an accelerometer;
an intracardiac impedance sensor;
a transthoracic impedance sensor;
a temperature sensor, wherein the sensor signal is representative of body temperature of the subject; and
the cardiac signal sensing circuit, wherein the sensor signal includes a representation of a depolarization interval that includes a QRS complex.

16. The apparatus of claim 1, wherein the controller circuit is configured to initiate pacing at the device-indicated rate or set the pacing rate below the sensed intrinsic rate when a specified pacing rate is reached during the monitoring or when the AV interval of the subject becomes unstable during the monitoring.

17. The apparatus of claim 1, wherein the chronotropic incompetence detection circuit is configured to continue to increase the pacing and monitor the AV interval until the AV interval of the subject becomes unstable during the monitoring, wherein the controller circuit is configured to store at least one of the rate or the interval at which the atrium is paced when the AV interval becomes unstable, and wherein only AV intervals prior to the AV interval becoming unstable are deemed as valid AV intervals and are used to calculate the change in AV intervals between the highest paced rate and the lowest paced rate used in the monitoring.

18. A method comprising:
pacing an atrium of the subject with an implantable medical device (IMD) while monitoring with the IMD a time interval between a paced event in the atrium and a sensed intrinsic event in the ventricle (paced AV interval), wherein the paced rate is higher than a device-indicated rate or sensed intrinsic rate;
increasing the pacing rate while continuing the monitoring of the paced AV interval;
calculating with the MID a change in paced AV intervals between a highest paced rate used in the monitoring and a lowest paced rate used in the monitoring;
determining with the IMD that the paced AV intervals are evidence of chronotropic incompetence when the calculated change in the paced AV intervals exceeds a specified threshold AV interval change value; and
providing an indication of chronotropic incompetence to a user or process.

19. The method of claim 18, wherein determining that the AV intervals are evidence of chronotropic incompetence includes determining a severity of the chronotropic incompetence according to a comparison of the calculated change to a plurality of specified threshold AV interval change values.

20. The method of claim 18, including:
monitoring AV intervals as a function of paced rate,
wherein calculating a change in the AV intervals includes calculating a slope of the change in AV intervals, and wherein determining that the AV intervals are evidence of chronotropic incompetence includes determining that the AV intervals are evidence of chronotropic incompetence when the calculated slope exceeds a specified slope value.

* * * * *